US006083875A

United States Patent [19]

Sato et al.

[11] Patent Number: 6,083,875

[45] **Date of Patent: *Jul. 4, 2000**

[54] SOLID GLYPHOSATE FORMULATIONS

[75] Inventors: Tatsuo Sato, Tokyo; Masuo Kuchikata, Ryugasaki, both of Japan; Marc Emile Toussaint, Corroy-le-Grand, Belgium

[73] Assignee: Monsanto Company, St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/576,417

[22] Filed: Dec. 21, 1995

[30] Foreign Application Priority Data

Dec. 30, 1994 [EP] European Pat. Off. .............. 94870215

[51] Int. Cl.[7] ............................ A01N 25/30; A01N 57/26

[52] U.S. Cl. ............................................................ 504/127

[58] Field of Search ............................. 424/405; 504/127

[56] References Cited

U.S. PATENT DOCUMENTS 5,258,359 11/1993 Kassebaum et al. ................... 504/206
5,464,806 11/1995 Kassebaum et al. ................... 504/206
5,627,166 5/1997 Iwasaki ..................................... 514/78

FOREIGN PATENT DOCUMENTS 0448538 9/1991 European Pat. Off. .
0617894 10/1994 European Pat. Off. .
WO91/08666 6/1991 WIPO ............................ A01N 25/12

*Primary Examiner*—Peter F. Kulkosky
*Attorney, Agent, or Firm*—Howry Simon Arnold & White

[57] ABSTRACT

The present invention relates to a solid herbicidal composition comprising:

a) oxyfluorfen herbicide dissolved in at least i) a surfactant selected from alkoxylated acetylenic diol surfactants;

ii) a surfactant selected from polyoxyalkylene alkyl ether surfactants, and iii) an alkoxylated organosilicone based surfactant, iv) a phosphate solvent of low water solubility, the ratio by weight of phosphate solvent to oxyfluorfen being lower than 3 to 1; and b) a water-soluble salt of N-phosphonomethylglycine, and optionally c) an inorganic carrier, and to a process for the production thereof.

20 Claims, No Drawings

SOLID GLYPHOSATE FORMULATIONS

The present invention relates to improved solid formulations comprising glyphosate herbicide and oxyfluorfen herbicide.

Glyphosate (N-phosphonomethylglycine) is a widely used non-selective, highly effective herbicide. Glyphosate herbicide is normally used into form of a water soluble salt, preferably the isopropylamine salt, sodium salt or ammonium salt, of glyphosate. Liquid and solid formulations intended to be diluted or dissolved in a spray tank by a farmer, generally contain in addition to the glyphosate salt, a surfactant or a surfactant mixture which increases the biological effectiveness of the glyphosate herbicide.

Numerous studies have been made on the effect of surfactants on the herbicidal action of glyphosate. Wyrill and Burnside, Weed Science, Vol. 25 (1977), 275–287, for instance studied the effects of many different surfactants including examples from different classes of surfactant. Some classes of surfactant were more effective than others in enhancing the herbicidal effect of glyphosate (used as a solution of the isopropylamine salt). Wyrill and Burnside concluded that an effective surfactant is an important component of any glyphosate spray formulation. The authors also mention that "effectiveness of surfactant combinations is quite variable and difficult to predict—therefore, the indiscriminate addition of surfactants or wetting agents to glyphosate sprays which already contain a surfactant should be avoided".

Glyphosate herbicide is known to be a highly effective herbicide but the treated plants show visual symptoms at a relatively late stage. It has already been suggested in the art to apply glyphosate herbicide in combination with diphenyl ether type of herbicides such as e.g. oxyfluorfen, essentially in order to accelerate the appearance of visual symptoms and to improve broadleaf weed control.

Oxyfluorfen is 2-chloro-a,a,a-trifluoro-p-tolyl 3-ethoxy-4-nitrophenyl ether. Technical oxyfluorfen is a red to yellow solid having a melting point of 65–84° C. Oxyfluorfen is a selective herbicide applied by pre-emergence or postemergence applications to cotton, onions, peanuts, soybeans, sugarcane, trees and vegetables, controlling monocotyledonous and broad-leaved weeds.

EP-A-0 143 547 discloses a herbicidal composition containing glyphosate herbicide and an oxyfluorfen type herbicide.

EP-A-0 448 538 and EP-A-0 394 211 in its Example 12 disclose a process for the preparation of a solid formulation comprising N-phosphonomethylglycine or a water-soluble salt thereof and oxyfluorfen. According to EP-0 448 538 a liquid premix comprising oxyfluorfen, at least one surfactant, and water or solvents is prepared at a temperature of from 50° C. to 80° C., thus dissolving oxyfluorfen, and a second premix comprising N-phosphonomethylglycine or a water soluble salt thereof, an acid acceptor if appropriate and reground ammonium sulphate is formed, and both premixes are combined to form an extrudable composition, which is extruded and optionally dried. In examples 4–6, a solution of oxyfluorfen in surfactants is prepared, so that the particle size of the oxyfluorfen actually applied to the vegetation is reduced: when poured into the spray water, the granules dissolve and a herbicidally effective solution comprising oxyfluorfen at a particle size reduced to an extent never reached before, surfactants and glyphosate is obtained.

Upon extended storage, however, crystal growth tends to occur, under unfavorable conditions, in the solid product obtained according to the Examples of EP-A-0 448 538. Such crystals are oxyfluorfen crystals and do not dissolve or disperse when diluted in the spray water. Crystal formation is obviously undesirable because of possible clogging up of spray equipment and reduced bioefficacy, non-homogeneity of the spray mixture and because of a reduction in the concentration of oxyfluorfen in the spray.

The object of the present invention is to improve the process and the product obtained according to EP-0 448 538 in such a way as to inhibit the crystal formation or at least reduce the crystal formation upon storage to an extent where its impact on the agricultural use of the solid product is negligible.

It has been found that the problem of the invention can be solved by changing the organic phase, that is the oxyfluorfen premix.

According to the present invention, the solid herbicidal composition comprises (a) oxyfluorfen herbicide dissolved in at least:

i) a surfactant selected from alkoxylated acetylenic diol surfactants ii) a surfactant selected from polyoxyalkylene alkyl ether surfactants, iii) an alkoxylated organosilicone based surfactant, iv) a phosphate solvent of low water solubility, and v) optionally solvents other than (iv), the ratio by weight of total solvent content to oxyfluorfen being lower than 3 to 1;

and (b) N-phosphonomethylglycine and optionally a suitable acid acceptor, or a water-soluble salt of N-phosphonomethylglycine, and optionally (c) an inorganic carrier.

The solid composition of the present invention may be produced by:

a) preparing a solution of oxyfluorfen in at least:

i) a surfactant selected from alkoxylated acetylenic diol surfactants;

ii) a surfactant selected from polyoxyalkylene alkyl ether surfactants, iii) an alkoxylated organosilicone based surfactant, iv) a phosphate solvent of low water solubility, and v) optionally solvents other than iv), the ratio by weight of total solvent content to oxyfluorfen being lower than 3 to 1, at a temperature between 20° C. and 90° C., preferably 50° to 90° C.;

b) adding i) N-phosphonomethylglycine and optionally a suitable acid acceptor or a water-soluble salt of N-phosphonomethylglycine; and ii) optionally an inorganic carrier c) mixing the components in a mixer or kneader to form a dough, d) shaping the obtained dough, and c) optionally drying.

It has been noticed that, when using polyoxyalkylene alkyl ether surfactants, the combination of an alkoxylated acetylenic diol surfactant with a phosphate solvent is essential to prevent the oxyfluorfen crystal formation.

The phosphate solvent should show a low solubility in water preferably of less than 1%, in order to avoid the solvent escaping into the water phase, thus being less available to maintain the oxyfluorfen in solution. The phosphate solvent should not be volatile or should have low volatility to avoid the solvent being lost to the atmosphere.

For reasons of environmental acceptability of the composition of the invention, the solvent content should be as low as possible. Also, the more solvent is comprised in the composition, the more the solid composition is undesirably soft. Therefore, the ratio by weight of total solvent to oxyfluorfen should be lower than 3 to 1, and the ratio by weight of phosphate solvent to oxyfluorfen is preferably about 2 to 1.

Alkoxylated organosilicone surfactants are well known in the art. Reference is made here to EP-0 448 538 and EP-0 394 211 which disclose advantageous alkoxylated organosilicone surfactants, and to "Surfactants and Detersive Systems", Kirk-Othmer, Encyclopedia of Chemical Technology, 3rd Edition, 22, 260–377 (1983) as well as to the Union Carbide Corp. product literature.

Examples of alkoxylated organosilicone surfactants are surfactants of the SILWET series, such as SILWET (R) L-77.

Examples of polyoxyalkylene alkyl ether surfactants are polyoxyethylene polyoxypropylene2-ethylhexyl ethers (e.g. Newkalgen 4016 EHB), HOE S-3510 (a polyoxyethylene polyoxypropylene alkyl ether), Emalgen PS-334 (a polyoxyethylene polyoxypropylene stearyl ether).

A preferred example of an alkoxylated acetylenic diol surfactant is a polyethoxylated 2,4,7,9-tetramethyl-5-decyne-4,7-diol (e.g. Surfynol 465).

Preferred solvents are triaryl phosphates such as tricresyl phosphate or trixylenyl phosphate or a trialkoxyalkyl phosphate such as tributoxyethyl phosphate. The most preferred solvent used in combination with above preferred acetylenic diol surfactant and polyoxyalkylene alkyl ether surfactant is Santicizer 141 (by Monsanto), an alkyl diaryl phosphate.

When adding the glyphosate herbicide, one of skill in the art can either use a glyphosate salt, such as the isopropylamine salt or sodium salt or trimethylsulphonium salt or ammonium salt of glyphosate, or even a mixture thereof. One may also combine glyphosate in its acid form with a suitable acid acceptor known in the art, such as ammonia, ammonium hydroxide, ammonium acetate, ammonium carbonate, ammonium bicarbonate, sodium acetate, potassium acetate, sodium bicarbonate, sodium carbonate, sodium metaborate, sodium citrate, tetrasodium EDTA, sodium formate, sodium hydroxide, sodium oxalate, trisodium phosphate, tripotassium phosphate, sodium propionate, sodium pyrophosphate, sodium metasilicate, sodium orthosilicate, sodium sulfite, sodium thiosulfate, sodium tetraborate, dipotassium phosphate, diammonium phosphate, sodium tripolyphosphate, sodium metaphosphate, ammonium and potassium salts thereof, mixtures thereof and the like but more preferably the acid acceptor is selected from ammonium bicarbonate, sodium bicarbonate, diammonium phosphate, disodium phosphate and mixtures thereof. The glyphosate content (as acid equivalent) may be between 5 and 70% w/w of the formulation, preferably between 20 and 50% w/w.

Inert inorganic carriers such as ammonium sulfate, sodium sulfate, potassium sulfate, monoammonium phosphate, diammonium phosphate, monosodium phosphate or disodium phosphate may be used in a manner known per se. Preferably the ratio of inorganic carrier to glyphosate (calculated as acid equivalent) may be comprised between 0 and 10, preferably between 0 and 5.

The process of shaping may consist in a step known by the skilled person. In a preferred embodiment of the invention process, such a step consists in an extrusion step, preferably radial extrusion. Preferably, the mixing/kneading step may be performed in an extruder as well. Other shaping steps, like compression, pan granulation etc. . . may also be used.

If required, a drying step may be provided after the shaping of granules. Such a drying step may consist in a step known by the skilled person who will find the appropriate equipment without undue experimentation. A preferred dryer may consist in a fluid bed dryer.

According to this invention, the weight ratio of glyphosate acid equivalent to said oxyfluorfen is in the range of from 100:1 to 5:1, preferably of from 50:1 to 10:1.

In order not to inhibit the processability of the first premix (oxyfluorfen solution) as well as of the dough intended for granulation, preferably extrusion granulation, the optional solvent content of the first premix should generally be kept to a level as low as possible. Minor amounts of additional solvents may be present.

The compositions of the present invention or as obtained according to the process described hereabove do not show any crystal formation after 1 year at ambient temperature.

According to another aspect of the present invention, a method of use of the solid composition described above is concerned. The selected amount of herbicide containing N-phosphonomethylglycine and oxyfluorfen as the active ingredients to be employed is dependent upon the response desired in the plant, as well as such other factors as the plant species and the stage of development thereof, the amount of rainfall, as well as the specific composition employed. In foliar treatment for the control of vegetative growth, the active ingredients are applied in amounts from about 0.10 to 3 or more kg/ha. An effective amount for phytotoxic or herbicidal control is that amount necessary for overall control i.e. a phytotoxic or herbicidal amount. It is believed that one skilled in the art can readily determine from the teachings of this specification the approximate application rate. The solid formulation has first to be diluted in a water tank at the appropriate concentration, and then it may be sprayed at the appropriate rate on the plants to be treated.

It has to be pointed out that the solid formulation of this invention where the oxyfluorfen herbicide is in a surfactant/solvent solution, eventually forms a clear or translucent spray dilution when diluted with water in the spray tank. The composition of the present invention allows the finest particle size for the oxyfluorfen active ingredient to be sprayed on the unwanted vegetation.

The following examples are presented to illustrate the present invention, as well as some of the various embodiments of the invention. All percentages in the following examples are on a weight basis, unless otherwise indicated.

EXAMPLE 1

1. Preparation of the oxyfluorfen solution. A 2 liter vessel was charged with 62.5 g of technical grade (99%) oxyfluorfen, 385 g polyoxyethylene-polyoxypropylene-2-ethylhexyl ether, 220.5 g SILWET L-77, 166 g Surfynol 465, and 166 g trixylenyl phosphate. The vessel was heated gently in a water bath. The mixture was stirred for about 30 minutes at 80° C.
2. Preparation of a granular formulation: The oxyfluorfen solution prepared above was mixed with 1280 g of 86% (acid equivalent) monoammonium salt of glyphosate and 2720 g of ammonium sulfate, in a kneader. The mixture was mixed with 150 g of water for 10 minutes at room temperature and was kneaded for 30 minutes to make an extrudable dough. The dough was then extruded through a screen having 1 mm openings, intended for lateral (radial) extrusion. The resulting granules were dried using an electric fan dryer at 70° C. for one hour.

3. Finale granule composition:

| | |
|---|---|
| oxyfluorfen tech. (99%) | 1.25 (1.24 a-i) w % |
| polyoxyethylene-polyoxypropylene-2-ethylhexyl ether | 7.70 |
| Silwet L-77 | 4.41 |
| Surfynol 465 | 3.32 |
| Trixylenyl phosphate | 3.32 |
| Ammonium glyphosate (86% a.e.) | 25.60 (22.00 a.e.) |
| Ammonium sulphate powder | 54.40 |

EXAMPLE 2

A procedure similar to Example 1 was followed to prepare the following granular formulation:

| | |
|---|---|
| oxyfluorfen tech (99%) | 2.07 (2.05% a.i.) |
| polyoxyethylene-polyoxypropylene-2-ethylhexyl ether | 6.65 |
| Silwet L-77 | 0.95 |
| Surfynol 465 | 7.58 |
| Trixylenyl phosphate | 3.80 |
| Phenylxylylethane | 0.48 |
| Bis (α-methylbenzyl)xylene | 0.43 |
| Xylene based solvents | 0.04 |
| Ammonium salt of glyphosate (86% a.e.) | 42.00 (36.12% a.e.) |
| Ammonium sulphate powder | 36.00 |
| | 100.00 |

EXAMPLE 3

The procedure of Example 1 was followed to prepare the following granular formulation:

| | |
|---|---|
| oxyfluorfen Tech. (99%) | 1.25 (1.24%/ai) |
| polyoxyethylene-polyoxypropylene-2-ethylhexyl ether | 7.70 |
| Silwet L-77 | 4.41 |
| Surfynol 465 | 3.32 |
| Trixylenyl phosphate | 3.32 |
| ammonium glyphosate (86 % ae) | 42.00 (36.12% ae) |
| ammonium sulphate powder | 38.00 |
| TOTAL | 100.00 |

EXAMPLE 4

The procedure of Example 1 was followed to prepare the following granular formulation:

| | |
|---|---|
| oxyfluorfen Tech (99%) | 1.25 (1.24% ai) |
| polyoxyethylene-polyoxypropylene-2-ethylhexyl ether | 7.70 |
| Silwet L-77 | 4.41 |
| Surfynol 465 | 3.32 |
| Trixylenyl phosphate | 3.32 |
| Ammonium salt of glyphosate (86% ae) | 80.00 (68.8% ae) |
| Total | 100.00 |

EXAMPLE 5

The procedure of Example 1 was followed to prepare the following granular formulation:

| | |
|---|---|
| Oxyfluorfen (99%) | 2.02 |
| polyoxyethylene-polyoxypropylene-2-ethylhexyl ether | 6.60 |
| Silwet L-77 | 0.95 |
| Surfynol 465 | 7.50 |
| Xylene based solvent mix | 0.95 |
| Santicizer 141 (Monsanto) | 3.80 |
| Ammonium glyphosate (85%) | 42.35 |
| Ammonium Sulphate | 35.33 |
| Water | 0.50 |
| | 100.00 |

The granular composition disclosed hereabove was subjected to an ageing test, for evaluation of its storage stability.

Samples of the granular composition were stored at temperatures of −10° C., 0° C., +10° C., room temperature, +40° C. and +54° C. for extended periods of time up to about three months. After three months storage, no crystals or phase separation could be detected for any of the above samples stored at the corresponding temperatures.

Also, at regular intervals, aliquots of the individual samples were used to prepare 2.8% solutions in water which were allowed to stand at room temperature for extended periods of time (static stability test). No sedimentation was detected after a standing expressed in hours, as represented in the Table below.

The results obtained are presented in the Table following:

| storage period<br>storage T ° C. | 25 days | 36 days | 72 days | 107 days |
|---|---|---|---|---|
| −10 | 7 | 7 | 6 | 6 |
| 0 | 7 | 7 | 6 | 6 |
| +10 | 7 | 7 | 7 | 7 |
| R.T. | 7 | 7 | 7 | 7 |
| +40 | 7 | 7 | 7 | 7 |
| +54 | 7 | 7 | 7 | 7 |

In a dynamic stability test, a sample stored during eight (8) weeks at −10° C. is used to prepare a 2.8% (w/v) spray solution (16.6 g in 600 ml solution). The spray solution is circulated through a Watson-Marlow 503 S pump set at about 30 rpm. The return pipe is arranged at about 10 cm above the spray solution which is agitated by means of a 4 blade propeller turning at a speed of about 100 rpm.

After an overnight recirculation, no particles could be detected on a 100 mesh sieve.

What is claimed is:

1. A solid herbicidal composition comprising:

(a) oxyfluorfen herbicide a surfactant selected from alkoxylated acetylenic diol surfactants;

a surfactant selected from polyoxyalkylene alkyl ether surfactants;

an alkoxylated organosilicone based surfactant having a formula selected from the group consisting of:

(A)

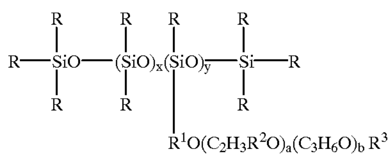

where each R is independently a monovalent hydrocarbyl radical, $R^1$ is a divalent hydrocarbylene radical, $R^2$ is independently hydrogen or a lower alkyl or hydroxyalkyl radical, $R^3$ is hydrogen or a monovalent hydrocarbyl radical, and x, y, a, and b are integers independently greater than or equal to zero;

(B)

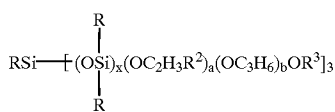

where R, $R^2$, and $R^3$, x, a, and b are as defined above;

(C)

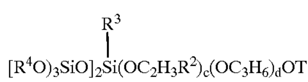

where $R^2$ and $R^3$ are as defined above, each $R^4$ group is independently a monovalent hydrocarbyl radical, c is at least four, d is greater than or equal to zero, and T is hydrogen, a monovalent alkyl or alkenyl radical, or a group of the formula $$—Si(R^3)[OSi(OR^4)_3]_2; \quad (D)$$

$$(R^4O)_3Si(OC_2H_3R^2)_e(OC_3H_6)_fOT^1$$

where $R^2$ and $R^4$ are as defined above, e is at least four, f is greater than or equal to zero, and $T^1$ is hydrogen, a monovalent alkyl or alkenyl radical, or a group of the formula $—Si(OR^4)_3$; and $$R^5[—(OC_2H_3R^2)_g\ OH]_{1-3} \quad (E)$$

where $R^2$ is as defined above, $R^5$ is a saturated or unsaturated alkyl or alkylphenyl radical having at least seven carbon atoms, and g is greater than or equal to one, a phosphate solvent having water solubility below 1%, selected from the group consisting of triaryl phosphates, trialkoxyalkyl phosphates, and alkyldiaryl phosphates, the ratio by weight of total solvent to oxyfluorfen being lower than 3 to 1;

(b) N-phosphonomethylglycine or a water-soluble salt of N-phosphonomethylglycine, wherein the weight ratio of glyphosate acid equivalent to said oxyfluorfen is in the range of from 100:1 to 5:1; and (c) an inorganic carrier wherein the combination of the polyoxyalkylene alkyl ether surfactant and the alkoxylated acetyleneic diol surfactant are present in the phosphate solvent in amounts to prevent oxyfluorfen crystal formation during storage of said solid herbicidal composition for three months at temperatures ranging from −10° C. to 54° C.

2. The solid herbicidal composition of claim 1 wherein the ratio by weight of phosphate solvent to oxyfluorfen is about 2/1.

3. The solid herbicidal composition of claim 1 wherein the alkoxylated acetylenic diol surfactant is a polyethoxylated 2,4,7,9-tetramethyl-5-decyne-4,7-diol.

4. A solid herbicidal composition of claim 1 wherein the weight ratio of glyphosate acid equivalent to said oxyfluorfen is in the range of from 50:1 to 10:1.

5. A method for killing or controlling unwanted vegetation comprising the step of applying to the said vegetation a herbicidally effective amount of the composition of claim 1.

6. The solid herbicidal composition of claim 1 further comprising a solvent other than the phosphate solvent.

7. The solid herbicidal composition of claim 1 further comprising an inorganic carrier selected from the group consisting of ammonium sulfate, monoammonium phosphate, diammonium phosphate, monosodium phosphate and disodium phosphate.

8. The solid herbicidal composition of claim 7 wherein the inorganic carrier is ammonium sulphate.

9. The solid herbicidal composition of claim 1 further comprising a suitable acid acceptor selected from the group consisting of ammonia, ammonium hydroxide, ammonium acetate, ammonium carbonate, ammonium bicarbonate, sodium acetate, potassium acetate, sodium bicarbonate, sodium carbonate, sodium metaborate, sodium citrate, tetrasodium ethylenediaminetetracetate, sodium formate, sodium hydroxide, sodium oxalate, trisodium phosphate, tripotassium phosphate, sodium propionate, sodium pyrophosphate, sodium metasilicate, sodium orthosilicate, sodium sulfite, sodium thiosulfate, sodium tetraborate, dipotassium phosphate, diammonium phosphate, sodium tripolyphosphate, sodium metaphosphate, ammonium and potassium salts thereof, and mixtures thereof.

10. A solid herbicidal composition comprising:

(a) oxyfluorfen, said oxyfluorfen having been combined with an alkoxylated acetylenic diol surfactant; a polyoxyalkylene alkyl ether surfactant;

an alkoxylated organosilicone based surfactant having a formula selected from the group consisting of:

(A)

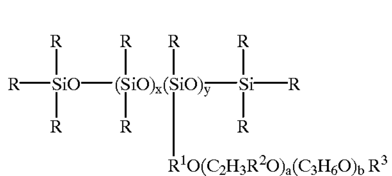

where each R is independently a monovalent hydrocarbyl radical, $R^1$ is a divalent hydrocarbylene radical, $R^2$ is independently hydrogen or a lower alkyl or hydroxyalkyl radical, $R^3$ is hydrogen or a monovalent hydrocarbyl radical, and x, y, a, and b are integers independently greater than or equal to zero;

(B)

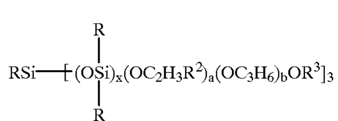

where R, $R^2$, and $R^3$, x, a, and b are as defined above;

(C)

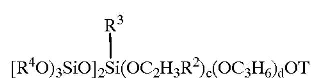

where $R^2$ and $R^3$ are as defined above, each $R^4$ group is independently a monovalent hydrocarbyl radical, c is at least four, d is greater than or equal to zero, and T is hydrogen, a monovalent alkyl or alkenyl radical, or a group of the formula $—Si(R^3)[OSi(OR^4)_3]_2$;

$$(R^4O)_3\ Si\ (OC_2H_3R^2)_e(OC_3H_6)_fOT^1 \quad (D)$$

where $R^2$ and $R^4$ are as defined above, e is at least four, f is greater than or equal to zero, and $T^1$ is hydrogen, a monovalent alkyl or alkenyl radical, or a group of the formula $—Si(OR^4)_3$ ; and $$R^5[—(OC_2H_3R^2)_g\ OH]_{1\text{-}3} \quad (E)$$

where $R^2$ is as defined above, $R^5$ is a saturated or unsaturated alkyl or alkylphenyl radical having at least seven carbon atoms, and g is greater than or equal to one; and a phosphate solvent having water solubility below 1%, selected from the group consisting of triaryl phosphates, trialkoxyalkyl phosphates, and alkyldiaryl phosphates, the ratio by weight of total solvent to oxyfluorfen being lower than 3 to 1;

(b) N-phosphonomethylglycine or a water-soluble salt of N-phosphonomethylglycine, wherein the weight ratio of glyphosate acid equivalent to said oxyfluorfen is in the range of from 100:1 to 5:1;and (c) an inorganic carrier wherein said solid herbicidal composition possesses the property of after three months of storage at temperatures ranging from −10° C. to 54° C., no crystal formation or phase separation occurs.

11. A solid herbicidal composition comprising:

(a) oxyfluorfen, said oxyfluorfen having been combined with an alkoxylated acetylenic diol surfactant; a polyoxyalkylene alkyl ether surfactant;

an alkoxylated organosilicone based surfactant having a formula selected from the group consisting of:

(A)

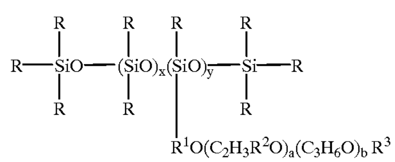

where each R is independently a monovalent hydrocarbyl radical, $R^1$ is a divalent hydrocarbylene radical, $R^2$ is independently hydrogen or a lower alkyl or hydroxyalkyl radical, $R^3$ is hydrogen or a monovalent hydrocarbyl radical, and x, y, a, and b are integers independently greater than or equal to zero;

(B)

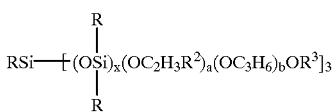

where R, $R^2$, and $R^3$, x, a, and b are as defined above;

(C)

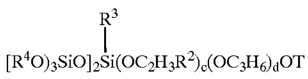

where $R^2$ and $R^3$ are as defined above, each $R^4$ group is independently a monovalent hydrocarbyl radical, c is at least four, d is greater than or equal to zero, and T is hydrogen, a monovalent alkyl or alkenyl radical, or a group of the formula

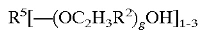

$$(R^4O)_3\ Si\ (OC_2H_3R^2)_e\ (OC_3H_6)_fOT^1 \quad (D)$$

where $R^2$ and $R^4$ are as defined above, e is at least four, f is greater than or equal to zero, and $T^1$ is hydrogen, a monovalent alkyl or alkenyl radical, or a group of the formula $—Si(OR^4)_3$; and $$R^5[—(OC_2H_3R^2)_gOH]_{1\text{-}3} \quad (E)$$

where $R^2$ is as defined above, $R^5$ is a saturated or unsaturated alkyl or alkylphenyl radical having at least seven carbon atoms, and g is greater than or equal to one; and a phosphate solvent having water solubility below 1%, selected from the group consisting of triaryl phosphates, trialkoxyalkyl phosphates, and alkyldiaryl phosphates, the ratio by weight of total solvent to oxyfluorfen being lower than 3 to 1;

wherein the alkoxylated acetylenic diol surfactant and the polyoxyalkylene alkyl ether surfactant and the phosphate solvent are present in amounts to prevent oxyfluorfen crystal formation during storage of said solid herbicidal composition for a period of three months at temperatures ranging from −10° C. to 54° C.;

(b) N-phosphonomethylglycine or a water-soluble salt of N-phosphonomethylglycine, and (c) an inorganic carrier.

12. A solid herbicidal composition comprising:

(a) oxyfluorfen combined with ethoxylated-2,4,7,9-tetramethyl-5-decyn-4,7-diol;

polyoxyethylene-polyoxypropylene-2-ethylhexyl ether;

a mixture of polyalkyleneoxide modified heptamethyltrisiloxane and allyloxypolyethyleneglycol methyl ether a phosphate solvent having water solubility below 1%, selected from the group consisting of tricresyl phosphate trixylenyl phosphate, tributoxyethyl phosphate and 2-ethylhexyl diphenyl phosphate and trialkoxyalkyl phosphates, and alkyldiaryl phosphates, the ratio by weight of total solvent to oxyfluorfen being lower than 3 to 1, (b) N-phosphonomethylglycine or a water-soluble salt of N-phosphonomethylglycine, and (c) an inorganic carrier wherein said solid herbicidal composition possesses the property of after three months of storage at temperatures ranging from −10° C. to 54° C., no crystal formation or phase separation occurs.

13. A solid herbicidal composition produced by the process of:

preparing an oxyfluorfen solution including:

oxyfluorfen;

a surfactant selected from alkoxylated acetylenic diol surfactants;

a surfactant selected from polyoxyalkylene alkyl ether surfactants;

an alkoxylated organosilicone based surfactant having a formula selected from the group consisting of:

(A)

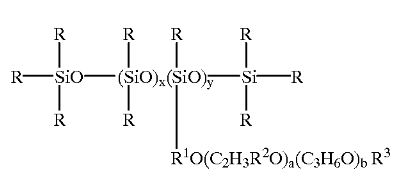

where each R is independently a monovalent hydrocarbyl radical, $R^1$ is a divalent hydrocarbylene radical, $R^2$ is independently hydrogen or a lower alkyl or hydroxyalkyl radical, $R^3$ is hydrogen or a monovalent hydrocarbyl radical, and x, y, a, and b are integers independently greater than or equal to zero;

(B)

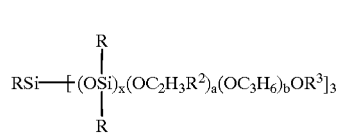

where R, $R^2$, and $R^3$, x, a, and b are as defined above;

(C)

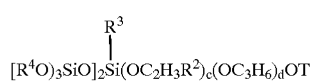

where $R^2$ and $R^3$ are as defined above, each $R^4$ group is independently a monovalent hydrocarbyl radical, c is at least four, d is greater than or equal to zero, and T is hydrogen, a monovalent alkyl or alkenyl radical, or a group of the formula $$—Si(R^3)[OSi(OR^4)_3]_2; \quad (D)$$

$$(R^4O)_3Si(OC_2H_3R^2)_e(OC_3H_6)_fOT^1$$

where $R^2$ and $R^4$ are as defined above, e is at least four, f is greater than or equal to zero, and T/ is hydrogen, a monovalent alkyl or alkenyl radical, or a group of the formula $-Si(OR^4)_3$ ; and $$R^5[—(OC_2H_3R^2)_gOH]_{1-3} \quad (E)$$

where $R^2$ is as defined above, R is a saturated or unsaturated alkyl or alkylphenyl radical having at least seven carbon atoms, and g is greater than or equal to one; and a phosphate solvent having water solubility below 1%, selected from triaryl phosphate trialkoxyalkyl phosphate or alkydiaryl phosphate, the ratio by weight of total solvent to oxyfluorfen being lower than 3 to 1, wherein the alkoxylated acetylenic diol surfactant and the polyoxyalkylene alkyl ether surfactant are present in the oxyfluorfen solution in amounts to prevent oxyfluorfen crystal formation during storage of said solid herbicidal composition for more than three months at temperatures ranging from −10° C. to 54° C., mixing said oxyfluorfen solution with N-phosphonomethylglycine or a water soluble salt of n-phosphonomethylglycine and optionally an inorganic carrier to form a dough;

shaping the dough; and optionally drying said dough.

14. The solid herbicidal composition of claim 13 wherein the shaping step is c out in an extruder, by radial extrusion.

15. The solid herbicidal composition of claim 13 wherein the constituents at step (b) are combined with the oxyfluorfen solution in an extruder.

16. The solid herbicidal composition of claim 13 wherein the drying step is carried out in a fluid bed dryer.

17. The solid herbicidal composition of claim 13 wherein the ratio by weight of phosphate solvent to oxyfluorfen is about 2/1.

18. The solid herbicidal composition of claim 13 wherein the alkoxylated acetylenic diol surfactant is a polyethoxylated 2,4,7,9-tetramethyl-5-decyne-4,7-diol.

19. The solid herbicidal composition of claim 13 wherein the inorganic carrier is ammonium sulphate.

20. A solid herbicidal composition of claim 13 wherein the weight ratio of glyphosate acid equivalent to said oxyfluorfen is in the range of from 100:1 to 5:1, preferably from 50:1 to 10:1.

* * * * *

UNITED STATES PATENT AND TRADEMARK OFFICE

CERTIFICATE OF CORRECTION

PATENT NO. : 6,083,875

DATED : July 4, 2000

INVENTOR(S) : Tatsuo Sato; Masuo Kuchikata; Marc Emile Toussaint

It is certified that error appears in the above-identified patent and that said Letters Patent is hereby corrected as shown below:

On the title page, Item [73] please delete "Monsanto Company, St. Louis, Mo." and insert -- Monsanto Europe S.A., Brussels Belgium --.

Signed and Sealed this

Second Day of January, 2001

Attest:

Q. TODD DICKINSON

Attesting Officer

*Commissioner of Patents and Trademarks*